United States Patent [19]

Drehman et al.

[11] 4,035,433

[45] July 12, 1977

[54] SELECTIVE OXIDATION OF ACETYLENES

[75] Inventors: Lewis E. Drehman; Thomas Davis, both of Bartlesville, Okla.

[73] Assignee: Phillips Petroleum Company, Bartlesville, Okla.

[21] Appl. No.: 704,884

[22] Filed: July 13, 1976

[51] Int. Cl.² .......................................... C07C 7/02
[52] U.S. Cl. ................... 260/681.5 R; 260/677 R; 260/677 A
[58] Field of Search .................. 260/681.5, 677

[56] References Cited

U.S. PATENT DOCUMENTS

| | | | |
|---|---|---|---|
| 2,381,707 | 8/1945 | Wood et al. | 260/677 A |
| 2,398,301 | 4/1946 | Frevel | 260/681.5 |
| 2,964,579 | 12/1960 | Kirsch | 260/677 |
| 2,969,407 | 1/1961 | Rosenberg et al. | 260/681.5 |
| 3,108,947 | 10/1963 | Stijntjes | 208/144 |
| 3,202,727 | 8/1965 | Dancer | 260/681.5 |
| 3,218,268 | 11/1965 | Arnold | 252/465 |
| 3,274,286 | 9/1966 | Reich | 260/681.5 |
| 3,297,776 | 1/1967 | Reich | 260/681.5 |
| 3,439,060 | 4/1969 | Kempton | 260/681.5 |

OTHER PUBLICATIONS

Kirk–Othmer, Ency. Chem. Tech. 2nd Ed. vol. 5, p. 496, 1965.
Kirk–Othmer, Ency. Chem. Tech. 2nd Ed. vol. 6, p. 270, 1965.
Sneed et al., Comprehensive Inorganic Chem. Van Nostrand, vol. 2, pp. 96–97, 1954.

*Primary Examiner*—Veronica O'Keefe

[57] ABSTRACT

Acetylenic compounds are selectively removed from hydrocarbon mixtures containing same by oxidation in the presence of a copper chromite catalyst. In one embodiment, acetylenic compounds are selectively removed from streams containing $C_4$ unsaturated hydrocarbons containing same by contacting oxygen and the stream with a catalyst of copper, chromium, and oxygen under oxidizing conditions.

7 Claims, No Drawings

SELECTIVE OXIDATION OF ACETYLENES

This invention relates to the purification of unsaturated hydrocarbon-containing mixtures to remove undesirable contaminants therefrom. In accordance with one aspect, this invention relates to a method of removing unsaturants such as acetylenes from hydrocarbon mixtures containing same by contacting the mixture and oxygen at an elevated temperature with a copper chromite catalyst. In accordance with a further aspect, this invention relates to a process for the purification of $C_4$ unsaturated hydrocarbon-containing mixtures also containing acetylenic compounds as impurities by contacting at an elevated temperature with the copper, chromium, and oxygen catalyst under oxidizing conditions. In accordance with a further aspect, this invention relates to a process for the purification of the effluent from an oxidative dehydrogenation process for converting $C_4$ hydrocarbons by oxidizing the effluent with a copper chromite catalyst to selectively remove acetylenic compounds therefrom.

The present invention provides a method whereby acetylenes such as vinylacetylene, methylacetylene, 1-butyne, and the like can be selectively removed from hydrocarbon mixtures containing same, especially conjugated diene mixtures containing them, without the necessity for hydrogenation and extensive fractionation. There is thus provided a means whereby substantial reduction and planned investment in utility is realized.

The invention relates more specifically to a process for removing acetylenic compounds (impurities) found in small amounts, i.e., 0.01–3 mole percent, in refinery streams comprising paraffins, olefins, diolefins, water, nitrogen, oxygen, etc. The product gas stream obtained by the vapor phase catalytic oxidation of butenes to form butadiene is a typical stream which can be treated by the process of the present invention. Such a gas stream contains, in addition to butadiene, unreacted butene, water, oxygen, nitrogen, carbon dioxide, carbon monoxide, and traces of acetylenes. The presence of acetylenes in the product is most undesirable, causing difficulties in the subsequent separation of butadiene from unreacted butenes and being an unacceptable impurity in the final product.

It has now been found that by selective oxidation in the presence of a copper chromite catalyst it is possible to remove the acetylenes from such gaseous streams without significant loss of unsaturated hydrocarbons such as butadiene by oxidation.

Accordingly, an object of this invention is to provide a simplified process for removing acetylenes from unsaturated hydrocarbon-containing mixtures such as conjugated diene streams.

Another object of this invention is to provide an improved process for removing acetylenes from conjugated diene-containing mixtures to provide a highly purified conjugated diene-containing stream.

A further object of this invention is to provide a process for purification of conjugated diene streams obtained from oxidative dehydrogenation processes whereby acetylenic contaminants are removed therefrom.

Further objects, aspects, and the several advantages of the invention will be apparent to those skilled in the art upon a study of the disclosure and the appended claims.

According to the present invention, a process for the removal by selective oxidation of acetylenic compounds from a gas stream containing same is provided which comprises passing the gas stream in admixture with sufficient oxygen over a copper chromite catalyst under conditions of temperature and pressure sufficient to remove a substantial portion of the acetylenes present without destroying significant amounts of desirable unsaturated hydrocarbons present in the stream treated.

More specifically, according to this invention, acetylenic compounds in hydrocarbon-containing streams such as butadiene-containing streams are removed by selective oxidation under reaction conditions in the presence of free oxygen by contacting with a copper-chromium-oxygen catalyst.

In actual operation, small amounts of acetylenes, i.e., 0.01–3 mole percent, contained in refinery streams or other hydrocarbon streams comprising olefins, diolefins, paraffins, water, nitrogen, oxygen, etc., are selectively removed under reaction conditions with the catalyst of this invention. Diolefins are often the predominating component in such streams. The acetylenes are selectively oxidized to water and carbon oxides in the presence of molecular oxygen by contact with a solid catalyst of copper, chromium, and oxygen. Diluents such as steam and other fluids inert in the process such as nitrogen, argon, helium, and the like can also be admixed with the feed.

The catalyst of this invention can be prepared by mixing together copper oxide and chromium oxide or compounds which produce such oxides on calcination. For example, the hydroxides of the metals can be co-precipitated by the addition of a solution of a soluble hydroxide to a solution containing the dissolved metal salts. The precipitate is washed to remove soluble impurities, and the product is calcined in air to convert the hydroxides to the oxides which then may further react to form copper chromite, $CuCr_2O_4$, a mixture of $CuCr_2O_4$ and $CuO$, or $Cu_2Cr_2O_4$, and mixtures thereof. The atom ratio of Cu:Cr in the compositions can vary from about 0.3:1 to about 1:1 and is preferably about 0.5:1. As demonstrated by the specific working example described hereinafter, one particularly effective catalyst composition that has been used contains about 28 weight percent copper, about 45 weight percent chromium, with the balance being combined oxygen. The compounds are described more fully in Comprehensive Inorganic Chemistry, Vol. II, pages 96, 97, and in Encyclopedia of Chemical Technology, Kirk-Othmer, Ed. II, Vol. 5, page 496, for example.

The products, after calcining and cooling, are generally ground and screened and used in the form of particles ranging in size from about 4 to about 40 mesh based on U.S. Sieve series. If desired, the powdered catalyst can be formed by conventional pelleting practices with the aid of lubricants such as polyethylene into pellets, wafers, cylinders, etc., ranging in size from about 1/32 to ½ inch (0.08–1.3 cm). Generally, the pelleted material is recalcined to remove the lubricant. The finished catalyst can be used as is or ground and screened again. It usually has a surface area ranging from about 1 to about 40 square meters per gram and an apparent bulk density of about 1.5 to about 2 g/cc.

The process of the invention can be carried out under a wide range of oxidation conditions, depending upon feedstock and desired degree of acetylenes removal. Broadly, the conditions of temperature, pressure, and amounts of oxygen present during the oxidation reaction will be sufficient to selectively remove a substantial portion of the acetylenic compounds present in the feedstock being treated without any appreciable loss of other unsaturated hydrocarbons by oxidation. The reaction can be carried out in any suitable apparatus, either continuously or batchwise. Continuous operation through a fixed catalyst bed is the presently preferred mode of reaction.

Process conditions suitable in practicing the invention include reaction temperatures ranging from about 400°–800° F (204°–427° C), more preferably from about 550°–650° F (288°–343° C); reaction pressures ranging from about 0.5–500 psig (3.4–3447 kPa gage), more preferably from about 5–100 psig (34–689 kPa gage); an oxygen to hydrocarbon mole ratio ranging from about 0.01–0.2, more preferably from about 0.02–0.12; and a stream to hydrocarbon mole ratio of 0 to 100, more preferably from about 5 to 50. Hydrocarbon feed rates can change from about 50 to about 5000 gaseous hourly space velocity (GHSV).

The catalyst can be regenerated by shutting off the feed and passing air, optionally admixed with steam, over the catalyst at temperatures at least as high as the reaction temperature and preferably about 100° F higher or even more.

EXAMPLE

A cupric chromite catalyst was prepared by coprecipitation of a solution containing 242 g of Cu(NO$_3$)$_2$.3H$_2$O and 800 g of Cr(NO$_3$)$_3$.9H$_2$O dissolved in 550 cc of deionized water with a caustic solution containing 320 g NaOH dissolved in 250 cc of deionized water to a final pH of about 10. The mixture was stirred about 1½ hours and filtered. The precipitate was washed three times with 500 cc portions of deionized water, dried 16 hours at 225° F (107° C), and calcined about 3.5 hours in air at 650° F (343° C). The resulting material was ground, mixed with 3 weight percent polyethylene powder as lubricant and pilled at 400 psig (2758 kPa gage). The pills were calcined in air for four hours at 1100° F (593° C), cooled, ground, and screened to obtain 20–40 mesh particles. Analysis of the catalyst gave 27.9 weight percent copper and 44.5 weight percent chromium, the balance being combined oxygen. The catalyst had a surface area of 1.9 square meters/g, an apparent bulk density of 1.74 g/cc, and a pore volume of 0.15 cc/g.

A hydrocarbon stream consisting of 89.04 mole percent butadiene, 0.155 mole percent vinylacetylene, 10.48 mole percent butenes, 0.08 mole percent n-butane, and 0.01 mole percent neopentane was contacted in the presence of air with the catalyst and in the absence or presence of steam at a pressure of 10 psig (68.9 kPa gage). In each run, 3.00 cc (5.10 g) of the catalyst in the form of 20–40 mesh particles was charged to a tubular, fixed bed reactor. The conditions employed and results obtained are presented in the following Table.

TABLE

Oxidation of Vinylacetylene with Copper Chromite Catalyst

| Run No. | Catalyst Age (hrs.) | Feed GHSV | Reactor Temperature °F | Reactor Temperature °C | Mole Ratios Oxygen/Feed | Mole Ratios Steam/Feed | Conversions, % Vinyl-acetylene | Conversions, % Butadiene | Conversions, % Butenes |
|---|---|---|---|---|---|---|---|---|---|
| 1 | 8[a] | 1160 | 300 | 149 | 0.036 | 0 | −5.3[b] | 0.5 | 1.1 |
| 2 | 26[a] | 1120 | 400 | 204 | 0.031 | 0 | 1.3 | −0.4 | 5.0 |
| 3 | 30[a] | 1030 | 500 | 260 | 0.032 | 0 | 2.4 | −0.2 | 4.6 |
| 4 | 33 | 1060 | 600 | 316 | 0.031 | 0 | 74.2 | 1.2 | 0.3 |
| 5 | 34[a] | 1080 | 600 | 316 | 0.030 | 0 | 58.3 | 0.6 | 4.5 |
| 6 | 37 | 1070 | 600 | 316 | 0.031 | 12.3 | 89.2 | 0.5 | 0.9 |
| 7 | 38 | 1270 | 600 | 316 | 0.029 | 21.4 | 100.0 | 0.0 | 3.9 |
| 8 | 42[a] | 1310 | 600 | 316 | 0.023 | 13.3 | 100.0 | −0.2 | 5.6 |
| 9 | 44 | 1100 | 500 | 260 | 0.026 | 12.4 | 9.6 | −0.6 | 5.7 |
| 10 | 46 | 1210 | 600 | 316 | 0.031 | 17.0 | 100.0 | 1.3 | 4.6 |

Notes: [a]Catalyst regenerated after this test.
[b]Minus in results indicates that more compound found in effluent than in feed to reactor.
Analysis of the feed charged to the reactor and the effluent obtained is illustrated for Run 10.
All are in terms of mole percent.

| | Feed | Effluent | | Feed | Effluent |
|---|---|---|---|---|---|
| Oxygen | 2.73 | 0.04 | Butene-1 | 1.24 | 1.26 |
| Nitrogen | 9.74 | 9.37 | t-Butene-2 | 2.56 | 2.42 |
| Hydrogen | 0.0 | 0.0 | c-Butene-2 | 5.38 | 4.74 |
| Carbon monoxide | 0.0 | 0.04 | Butadiene | 77.94 | 74.03 |
| Carbon dioxide | 0.0 | 1.01 | C$_5$'s | 0.20 | 0.47 |
| Methane | 0.0 | 0.0 | Vinylacetylene | 0.136 | 0.0000 |
| Ethylene | 0.0 | 0.0 | Water | 0.0 | 3.12 |
| Propane | 0.0 | 0.06 | Coke (calculated) | 0.0 | 3.38 |
| Propylene | 0.0 | 0.0 | | | |
| Isobutane | 0.0 | 0.0 | | | |
| n-Butane | 0.07 | 0.07 | | | |
| Neopentane | 0.01 | 0.0 | | | |

Inspection of the results reveals that oxidation of vinyl acetylene in the absence of steam begins at about 400° F as Run 2 illustrates but that significant oxidation occurs at 600° F as Run 5 shows. Run 6 shows the catalyst appears to be sensitive to a slightly lower oxygen/feed ratio, even at 600° F, and as a result a lower amount of oxidation of vinylacetylene results than in Run 5.

When steam is included with the feed, its beneficial effects are shown in Runs 7, 8, and 10 as 100 percent oxidation of vinylacetylene is achieved in each run. Even in the presence of steam, the results in Run 9 clearly show that relatively poor oxidation of vinylacetylene occurs at a reactor temperature of 500° F. Thus, excellent results are obtained at 600° F with steam/feed mole ratios ranging from about 13:1 to 21:1 and oxygen/feed mole ratios ranging from about 0.02:1 to about 0.03:1.

The invention is not confined to the treatment of C$_4$ fractions containing butadiene although this is a preferred embodiment. Typical feedstreams which can be successfully treated according to the invention include commercial hydrocarbon-containing streams obtained in petroleum refining and cracking operations. Such streams usually contain alkanes of up to about five carbon atoms; olefins such as ethylene, propylene, butylene, and amylene; diolefins such as allene, butadiene, 1,3-dimethyl-allene, isoprene, and 1,3-pentadiene; and relatively minor amounts of acetylenic compounds such as acetylene, methylacetylene, ethylacetylene, vinylacetylene, etc., as well as some additional hydrocarbons and other organic compounds with more than five carbon atoms. Generally, acetylenic impurities such as those found in streams of corresponding hydrocarbons less highly unsaturated, for example, in streams consisting largely or in some part of the lower olefins and diolefins, are generally treated according to the invention. Of course, the acetylenic hydrocarbon impurities are also removable by the present catalyst from other gases such as air, inert purge gases, and the like.

We claim:

1. A process for the selective removal of acetylenic contaminants or impurities present in hydrocarbon streams which comprises contacting oxygen and a hydrocarbon-containing mixture contaminated with acetylenic compounds with a catalyst consisting essentially of copper, chromium, and oxygen in which the atomic ratio of copper to chromium varies from about 0.3:1 to about 1:1 under oxidation conditions including a temperature and a mole ratio of oxygen to hydrocarbon sufficient to selectively remove a substantial portion of said acetylenic compounds present in said mixture.

2. A process according to claim 1 wherein said contacting is effected at a temperature ranging from about 400°–800° F (204°–427° C), a reaction pressure ranging from 0.5–500 psig (3.4–3447 kPa gage), an oxygen to hydrocarbon mole ratio ranging from 0.01–0.2, a steam to hydrocarbon mole ratio of 0–100, and a hydrocarbon feed rate ranging from about 50 to about 5000 GHSV.

3. A process according to claim 1 wherein the mixture comprises $C_4$ unsaturated hydrocarbons and said contacting is effected in the presence of steam at a steam to hydrocarbon mole ratio of up to about 100.

4. A process according to claim 1 wherein said contacting is effected in the presence of air and steam at a steam to hydrocarbon mole ratio up to about 100 and at a temperature in the range of about 550°–650° F (288°–343° C).

5. A process according to claim 1 wherein said mixture is a hydrocarbon stream which contains oxygen, steam, and acetylenes, as well as butadiene and other $C_4$ hydrocarbons, and said contacting is effected at a temperature in the range of about 550°–650° F (288°–343° C).

6. A process according to claim 1 wherein the catalyst is a copper chromite ($CuCr_2O_4$) of about 28 weight percent copper, about 45 weight percent chromium, and the balance combined oxygen.

7. A process according to claim 1 wherein said catalyst is copper chromite ($CuCr_2O_4$) and said contacting is effected in the presence of air and steam at a steam to hydrocarbon mole ratio of about 10 to about 50 and at a temperature in the range of about 550°–650° F (288°–343° C).

* * * * *